United States Patent [19]

Beverung, Jr. et al.

[11] 3,983,119

[45] Sept. 28, 1976

[54] PROCESS FOR THE PREPARATION OF OPTIONALLY SUBSTITUTED 1,2,3,5-TETRAHYDROIMIDAZO[2,1-b]QUINAZOLIN-2-ONES

[75] Inventors: Warren Neil Beverung, Jr., Minoa; Richard Anthony Partyka; Thomas Andrew Jenks, both of Liverpool, all of N.Y.

[73] Assignee: Bristol-Myers Company, New York, N.Y.

[22] Filed: Nov. 6, 1974

[21] Appl. No.: 521,304

[52] U.S. Cl. .................... 260/256.4 F; 260/256.5 R; 424/251

[51] Int. Cl.² .................... C07D 187/04

[58] Field of Search .................... 260/256.4 F, 256.5 R

[56] References Cited

UNITED STATES PATENTS

| | | | |
|---|---|---|---|
| 3,257,401 | 6/1966 | Wagner | 260/256.4 F |
| 3,600,390 | 8/1971 | Sherlock | 260/256.4 F |
| 3,621,025 | 11/1971 | Jen et al. | 260/256.4 F |
| 3,745,216 | 7/1973 | Jen et al. | 424/251 |
| 3,790,576 | 2/1974 | DeWald | 260/286 R |
| 3,859,289 | 1/1975 | Hardtmann | 260/256.4 F |

FOREIGN PATENTS OR APPLICATIONS

| | | | |
|---|---|---|---|
| 2,081,375 | 12/1971 | France | |
| 2,305,575 | 8/1973 | Germany | 260/256.4 F |

OTHER PUBLICATIONS

Bernard, et al., "Chemical Abstracts," vol. 74, 1971, Col. 1418596.

Brown, Heterocyclic Compounds: Fused Pyrimidines, Part I, 1967, Wiley-Interscience, N.Y. pp. 222–225.

Cox, et al., "J. Chem. Soc. (c), 1970, pp. 2134–2136.

Beverung, et al., J. Med. Chem., vol. 18, 1975, pp. 224–225.

*Primary Examiner*—Nicholas S. Rizzo
*Assistant Examiner*—James H. Turnipseed
*Attorney, Agent, or Firm*—Robert E. Havranek

[57] ABSTRACT

A new process has been developed for the synthesis of optionally substituted 1,2,3,5-tetrahydroimidazo[2,1-b]quinazolin-2-ones. In particular, the process is particularly adaptable for the preparation of the 5,6-disubstituted compounds, e.g., 5,6-dimethyl-1,2,3,5-tetrahydroimidazo-[2,1-b]quinazolin-2-one. The compounds so prepared are useful as blood platelet anti-aggregative and/or antihypertensive agents in mammals, including humans.

4 Claims, No Drawings

PROCESS FOR THE PREPARATION OF OPTIONALLY SUBSTITUTED 1,2,3,5-TETRAHYDROIMIDAZO[2,1-B]QUINAZOLIN-2-ONES

BACKGROUND OF THE INVENTION

1. Field of the Invention

The compounds of the present invention are useful in the control of mild to severe hypertension, as platelet anti-aggregative agents and, in some instances, bronchodilators.

2. Description of the Prior Art

The compounds of the present invention are new and novel and so is the process described herein. The literature discloses the following prior art:

A. The compounds characterized as 1- and 9-alkyl-2,3-dihydroimidazo-[1,2-a]-benzimidazoles [R. J. North and A. R. Day, J. Hetro. Chem., 655 (1969)]. The compounds have the following structure

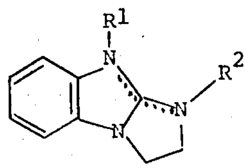

in which $R^1$ and $R^2$ are optionally substituted with alkyl functions.

B. B. Loev, T. Jen and R. A. McLean, Experientia, 27, 875 (1971) disclose the compound having the formula

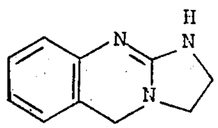

as having potent antihypertensive activity in rats, dogs, cats and rabbits.

C. R. Grout and M. Partridge, J. Chem. Soc., 3551 (1960) report the synthesis of the compound

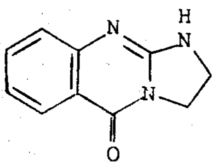

No antihypertensive activity was reported.

D. K. Lempert and G. Doleschall, Experientia, 18, 401 (1962) and Acta Chimica Academiae Scientiarum Hungaricae, 45, 357–68 (1965) report the synthesis of the compounds

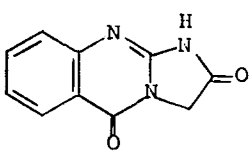

No antihypertensive activity was reported.

E. A. Simonov et al., Khim. Farmatseut. Zh., (1969) [Annual Reports in Medicinal Chemistry, Chapt. 6, 53 (1969)] report the preparation of 9-substituted imidazobenzimidazoles having the formula

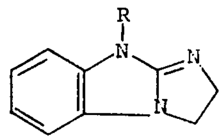

said compounds reported to have hypotensive effects in animals but no detailed data was presented.

F. G. E. Hardtmann, German Patent No. 2,025,248 (1970) reports bronchodilating the hypotensive effects for the compounds having the formula

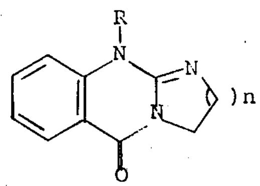

G. T. Jen et al., J. Med. Chem., 15 (7), 727–31 (1972) describe the compounds having the formula

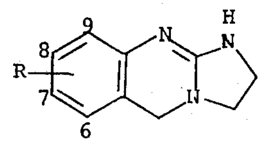

in which R is H, 6-Cl, 7-Cl, 7-MeO, 7-OH, 8-Cl, 9-Cl and 9-$CH_3$ as being hypotensive agents.

SUMMARY OF THE INVENTION

The compounds having the formula

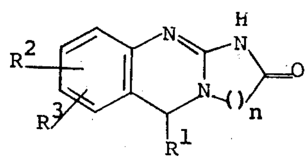

in which $R^1$ is (lower)alkyl of 1 to 6 carbon atoms, $R^2$ and $R_3$ are alike or different and are hydrogen, chloro, bromo, fluoro, $SO_3H$, $CF_3$, (lower)alkyl of 1 to 6 carbon atoms, hydroxy, nitro, amino, (lower)-alkoxy or phenyl, or when taken together $R^2$ and $R^3$ are methylenedioxy or the residue of a phenyl ring, and *n* is an integer of 1 or 2; are prepared by the process which comprises the consecutive steps of A. mixing a 2-aminoacetophenone having the formula

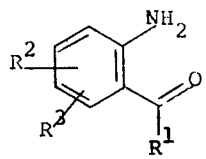

in which $R^1$, $R^2$ and $R^3$ are described above with a (lower)alkyl isocyanatoacetate having the formula

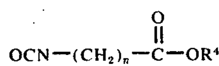

XII in which $R^4$ is (lower)alkyl of 1 to 6 carbon atoms, $n$ is 1 or 2 in a molar ratio of at least one mole of compound XII per mole of compound XI, preferably with the aid of heat, preferably in an organic solvent capable of forming an azeotrope, i.e., benzene, toluene, xylene and the like, separating the water so generated, to produce the compound having the formula

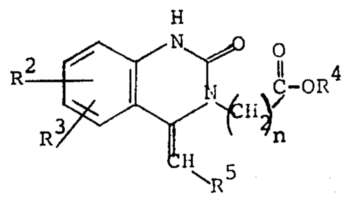

XIII in which $n$, $R^2$, $R^3$ and $R^4$ are as above and $R^5$ is H or (lower)alkyl of 1 to 5 carbons;

B. hydrogenating compound XIII with hydrogen in the presence of a metal catalyst, preferably palladium on charcoal in a (lower)alkanol-water solvent system, preferably methanol, ethanol or n-propanol to produce the compound having the formula

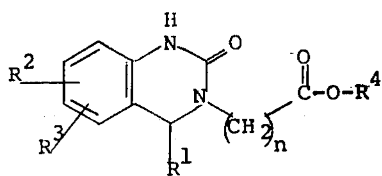

XIV in which $n$, $R^1$, $R^2$, $R^3$ and $R^4$ are as above;

C. halogenating compound XIV with a halogenating agent selected from the group consisting of $POBr_3$, phosphorous oxychloride, phosphorous pentachloride, thionyl chloride, etc. in a ratio of at least one mole of halogenating agent per mole of compound XIV, but perferably with a several fold excess of halogenating agent per mole of compound XIV, and preferably with phosphorous oxychloride, in the presence of a reaction inert solvent if needed, to produce the compound having the formula

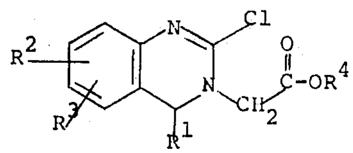

XV in which $R^1$, $R^2$ , $R^3$ and $R^4$ are as above; and

D. treating compound XV with large excess of ammonia dissolved in a (lower)alkanol, preferably methanol, ethanol, n-propanol or isopropanol, with the aid of heat, to produce the compounds I.

DETAILED DESCRIPTION

This invention relates to a new and improved process for the preparation of 1,2,3,5-tetrahydroimidazo [2,1-b]quinazolin-2-ones having the formula

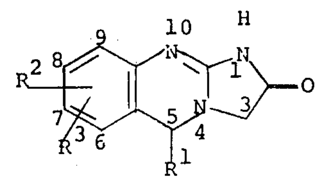

I in which $R^1$ is (lower)alkyl of 1 to 6 carbon atoms, $R^2$ and $R^3$ are alike or different and are hydrogen, chloro, bromo, flouro, $CF_3$, $SO_3H$, (lower)alkyl of 1 to 6 carbon atoms, hydroxy, nitro, amino, (lower)alkoxy or phenyl, or when taken together $R^2$ and $R^3$ are methylenedioxy or the residue of a phenyl ring; or a pharmaceutically acceptable acid addition salt thereof.

Hypertension is rather common and serious disease, particularly in elderly people. High blood pressure, a result of hypertension, is a common affliction. Most particularly hypertension is often the cause of crippling or fatal strokes in the elderly. It was, therefore, an object of the present invention to provide compounds useful in the treatment of mild to severe hypertension. prosthetic Subsequent to the preparation of some of the compounds of the present invention, it was found that most of the compounds also possessed unique properties as blood platelet anti-aggregative agents. These compounds are useful in the prevention of intravascular thromboses, prevention of coronary thrombosis, prevention of transient ischemic episodes, prevention of platelet thrombosis in the use of prosthetic devices (artificial heart valves, etc.). A large number of the compounds of the present invention have also been found to possess desirable bronchodilator activity in mammals.

For the purpose of this disclosure, the compounds of the present invention are represented as having the formulas I. However, compounds can exist in several possible tautomeric forms, e.g.:

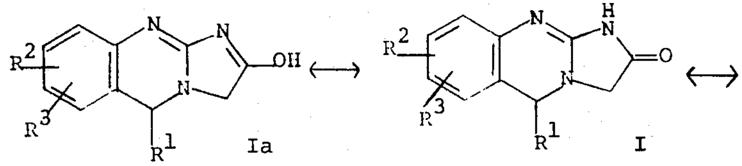

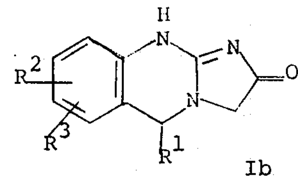

All the possible tautomers are considered an integral part of the present invention and all these forms are considered included when the compounds are represented as formula I.

The nontoxic salts that are pharmaceutically acceptable include the hydrochlorides, hydrobromides, hydroiodides, (lower)alkylsulfates, (lower)-alkyl and aryl sulfonates, phosphates, sulfates, maleates, fumarates, succinates, tartrates, citrates, and others commonly used in the art.

The salts obtained through the variation of the acid used in some cases have special advantage due to increased stability, increased solubility, decreased solubility, ease of crystallization, lack of objectionable taste, etc., but these are all subsidiary to the main physiological action of the free base, which is independent of the character of the acid used in the preparation of the salt.

Diagramatically the process of the instant invention is as follows:

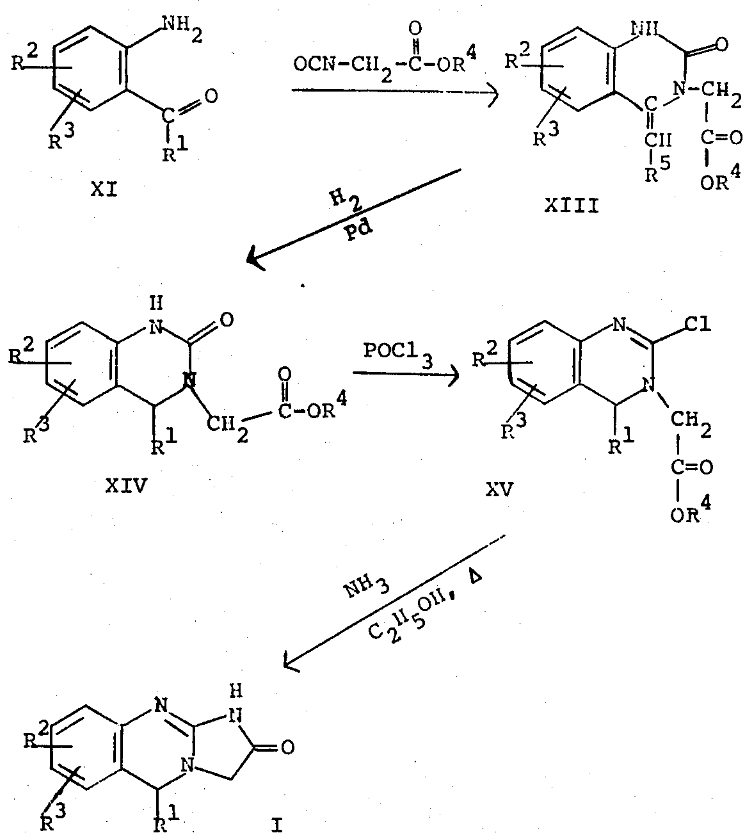

in which $R^1$, $R^2$, $R^3$, $R^4$ and $R^5$ are above.

In certain cases, particularly when $R^2$ or $R^3$ is a bromine or $NO_2$, it may be desirable to brominate or nitrate after producing compound I.

A preferred embodiment of the present invention is the process for the synthesis of compounds having the formula

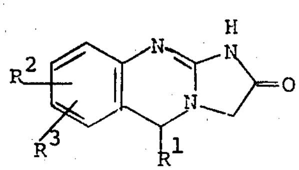

in which $R^1$ is (lower)alkyl, $R^2$ and $R^3$ are alike or different and are hydrogen, chloro, bromo, $SO_3H$, fluoro, (lower)alkyl, hydroxy, nitro, amino, (lower)alkoxy or phenyl, or when taken together $R^2$ and $R^3$ are methylenedioxy or the residue of a phenyl ring; which comprises the consecutive steps of A. mixing a 2-aminoacetophenone having the formula

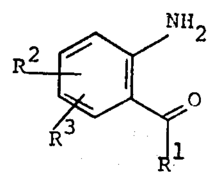
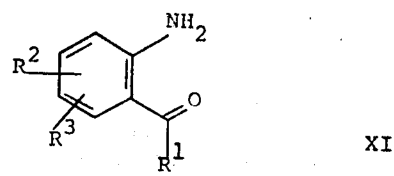

in which $R^1$, $R^2$ and $R^3$ are as described above, with a (lower)alkyl isocyanatoacetate having the formula

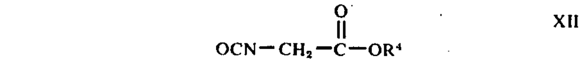

in which $R^4$ is (lower)alkyl of 1 to 6 carbon atoms, in a molar ratio of at least one mole of compound XII per mole of compound XI, with the aid of heat in the presence of a reaction inert organic solvent, to produce the compound having the formula

XIII in which $R^2$, $R^3$ and $R^4$ are as above and $R^5$ is H or (lower)alkyl of 1 to 5 carbon atoms;

B. hydrogenating compound XIII with hydrogen in the presence of a metal catalyst, in a (lower)-alkanol or water-(lower)alkanol solvent system to produce the compound having the formula

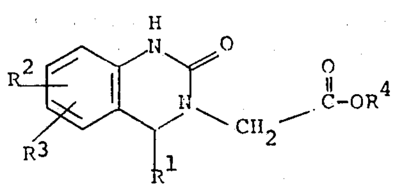

in which $R^1$, $R^2$, $R^3$ and $R^4$ are as above;

C. halogenating compound XIV with a halogenating agent, in a ratio of at least one mole of halogenating agent per mole of compound XIV, in the presence of a reaction inert organic solvent of needed, to produce the compound having the formula

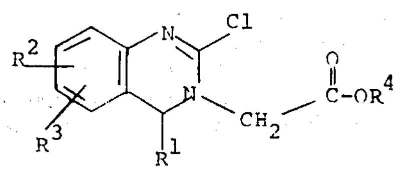

in which $R^1$, $R^2$, $R^3$ and $R^4$ are as above; and

D. treating compound XV with a large excess of ammonia, with the aid of heat, to produce the compounds of formula I.

A more preferred embodiment is the process for the preparation of compounds having formula I, which process comprises the consecutive steps of A. mixing a 2-aminoacetophenone having the formula

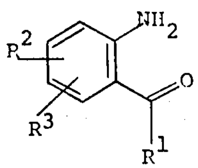

in which $R^1$ is (lower)alkyl, $R^2$ and $R^3$ are alike or different and are hydrogen, chloro, bromo, fluoro, (lower)alkyl, hydroxy, nitro, amino, (lower)alkoxy or phenyl, or when taken together $R^2$ and $R^3$ are methylenedioxy or the residue of a phenyl ring; with a (lower)alkyl isocyanatoacetate having the formula

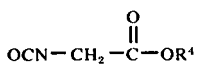

in which $R^4$ is (lower)alkyl of 1 to 3 carbon atoms in a molar ratio of about 1 to 1.5 moles of compound XII per mole of compound XI, in an organic solvent capable of forming an azeotrope, which solvent is selected from the group consisting of benzene, toluene, xylene and the like, separating the water so generated, to produce the compound having the formula

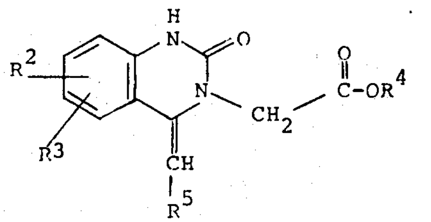

in which $R^2$, $R^3$, $R^4$ are as above and $R^5$ is H or (lower)alkyl of 1 to 5 carbon atoms;

B. hydrogenating compound XIII with hydrogen in the presence of a catalyst selected from the group consisting of palladium, platinum, Raney nickel, rhodium, ruthenium, nickel, and palladium on charcoal in a (lower)alkanol or (lower)alkanol-water solvent system, to produce the compound having the formula

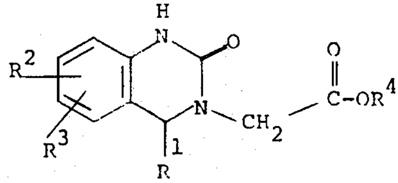

in which $R^1$, $R^2$, $R^3$ and $R^4$ are as above;

C. Chlorinating compound XIV with a chlorinating agent selected from he group consisting of phosphorous oxychloride, phosphorous pentachloride and thionyl chloride, in a ratio of at least one mole of chlorinating agent per mole of compound XIV, in the presence of a reaction inert organic solvent, if needed, to produce the compound having the formula

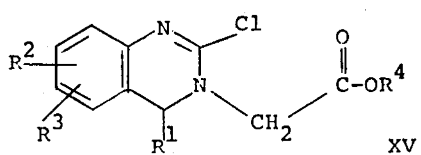

in which $R^1$,$R^2$, $R^3$ and $R^4$ are as above; and

D. treating compound XV with a large excess of ammonia dissolved in a (lower)alkanol, with the aid of heat in a sealed vessel to produce compound I.

A still further preferred embodiment is the process for the preparation of compounds having formula I, which process comprises the consecutive steps of A. mixing a 2-aminoacetophenone having the formula

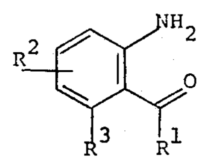

in which $R^1$ is (lower)alkyl of 1 to 3 carbon atoms, $R^2$ and $R^3$ are alike or different and are hydrogen, chloro, bromo, fluoro, (lower)alkyl of 1 to 3 carbon atoms, hydroxy, nitro, amino, (lower)alkoxy or phenyl, or when taken together $R^2$ and $R^3$ are methylenedioxy or the residue of a phenyl ring, with a (lower)alkyl isocyanatoacetate having the formula

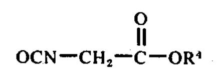

in which $R^4$ is (lower)alkyl of 1 to 2 carbon atoms in a molar ratio of about 1 to 1.2 moles of compound XII per mole of compound XI, in an organic solvent capable of forming an azeotrope, which solvent is selected from the group consisting of benzene, toluene, xylene and the like, separating the water so generated, to produce the compound having the formula

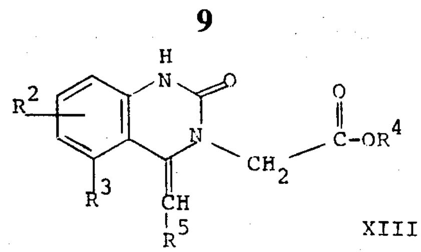

in which $R^2$, $R^3$, $R^4$ are as above and $R^5$ is H or (lower)alkyl of 1 to 2 carbon atoms;

B. hydrogenating compound XIII with hydrogen in the presence of a catalyst selected from the group consisting of palladium, platinum, Raney nickel, rhodium, ruthenium, nickel, and palladium on charcoal, in a (lower)alkanol or (lower)alkanol-water solvent system, to produce the compound having the formula

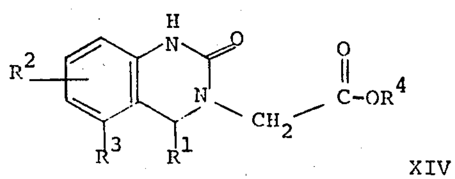

in which $R^1$, $R^2$, $R^3$ and $R^4$ are as above;

C. chlorinating compound XIV with a chlorinating agent selected from the group consisting of phosphorous oxychloride, phosphorous pentachloride and thionyl chloride, in a ratio of two to ten moles of chlorinating agent per mole of compound XIV, in the presence of a reaction inert organic solvent if needed, to produce the compound having the formula

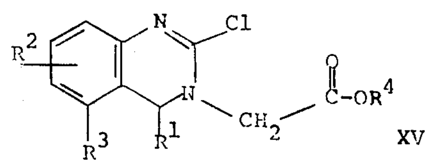

in which $R^1$, $R^2$, $R^3$ and $R^4$ are as above; and

D. treating compound XV with a large excess of ammonia dissolved in a (lower)-alkanol, with the aid of heat in a sealed vessel to produce compound I.

The most preferred embodiment is the process for the preparation of compounds having formula I, which process comprises the consecutive steps of A. heating a 2-aminoacetophenone having the formula

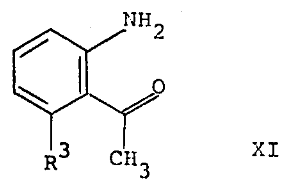

in which $R^3$ is methyl, methoxy or Cl, with a (lower)alkyl isocyanatoacetate having the formula

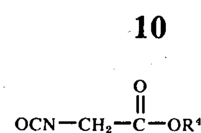

in which $R^4$ is methyl or ethyl in a molar ratio of about 1 to 1.1 moles of compound XII per mole of compound XI, in toluene at reflux temperature, separating the water so generated to produce the compound having the formula

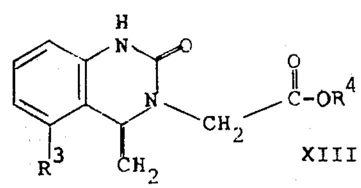

in which $R^3$ and $R^4$ are as above;

B. hydrogenating compound XIII with hydrogen in the presence of 5 to 10% palladium on charcoal, with mixing, in 95% ethanol, to produce the compound having the formula

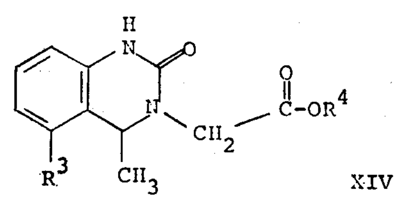

in which $R^3$ and $R^4$ are as above;

C. chlorinating compound XIV by dissolving it in a large molar excess of phosphorous oxychloride followed by heating at about 70° C. to about 115° C. for about 1 to 2 hours, following which the excess phosphorous oxychloride is removed in vacuo to produce the compound having the formula

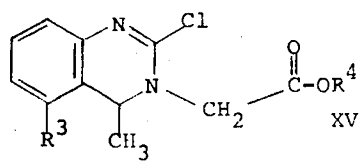

in which $R^3$ and $R^4$ are as above; and

D. heating compound XV with a large molar excess of ammonia dissolved in absolute ethanol in a sealed vessel at a temperature of about 100° C. to 110° C. to produce compound I having the formula

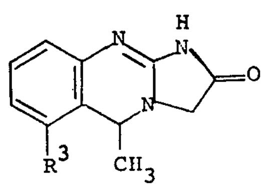

in which $R^3$ is as above;

For the purpose of this disclosure, the term (lower)alkyl shall mean straight and branched chain saturated aliphatic groups hving 1 to 6 carbons inclusive unless designated otherwise. The term (lower)alkanol or (lower)alkoxy shall have the same connotation, an alcohol or alkoxy group of 1 to 6 carbons inclusive.

Pharmacological evaluation has indicated the compounds produced by the present invention possess hypotensive activity.

The blood pressure of unanesthetized rats and dogs was measured directly by means of a transducer attached to an intra-arterial cannula and in anesthetized dogs by a mercury manometer attached to a carotid cannula.

The compounds of the instant invention were tested as the hydrochloride salts by the above method in genetically hypertensive rats in doses of 50 mg./kg. orally.

At the present time, indications are that the compounds do not appear to be acting in the same way as 2-(2,6-dichloroanilino)-2-imidazoline hydrochloride ["CATAPRES"]. Their activity is probably not attributable to α-adrenergic blockade or to ganglionic blocking action.

In the treatment of hypertension in animals including man, the compounds of the present invention are administered orally and/or parenterally, in accordance with conventional procedures for the administration of hypotensive agents in an amount of from about 0.5 mg./kg./dose to 30 mg./kg./dose depending upon the route of administration and the particular compound of the invention. The preferred dosage for the compounds of the invention is in the range of about 1.0 to 15.0 mg./kg./dose two to four times a day.

Pharmacological evaluation has also indicated the compounds of the present invention possess blood platelet anti-aggregative activity.

The aggregometer method of Born (1), as modified by Mustard et al. (2) was used to assess the in vitro activity of the various compounds as to inhibition of adenosine diphosphate (ADP) and collagen induced platelet aggregation. Platelet rich plasma was separated by centrifugation from citrated (3.8 per cent) rabbit blood. ADP in final concentration of 0.5 mcg./ml. or 0.05 ml. of a collagen suspension prepared according to the method described by Evans et al. (3) was used to induce aggregation. The various compounds tested were dissolved in dimethylsulfoxide (DMSO) so that 5 mcl. added to the platelet rich plasma would yield the desired test concentration. Vehicle control trails were done and compared with aggregation induced in platelet rich plasma containing various concentrations of the test compounds. Dose response curves were obtained and Effective Concentration (EC50) values calculated.

1. Born, G. V. R. J. Physiol., London, 162, 67P (1962).

2. Mustard, J. F., Hegardt, B. Rowsell, H. C. and MacMillan, R. L., J. Lab. Clin. Med. 64, 548 (1964).

3. Evans, G. Marian, M. C., Packham, M. A., Nishizawa, E. E., Mustard, J. F. and Murphy, E. A., J. Exp. Med., 128, 877 (1968).

Table I is illustrative of the hypotensive and blood platelet anti-aggregative activity of some of the preferred embodiments of the present invention.

TABLE I

| Compound No. | R Position 6 | 7 | 8 | 9 | Blood Pressure % Change Rats P.O. 50 mg./kg. | In Vitro $EC_{50}$ (mg./ml.) ADP | Collagen | In Vivo/In Vitro* Rabbits I.P. $ED_{50}$ (mg./kg.) ADP | Dogs P.O. 5 mg./kg. ADP % Inhibition |
|---|---|---|---|---|---|---|---|---|---|
| 1 | H | H | H | H | −36±6 | 6 | 2 | >72 | |
| 2 | Cl | H | H | H | −37±8 | 1 | 0.02 | 2 | |
| 3 | H | Cl | H | H | −4±5 | 0.5 | 0.2 | >10 | |
| 4 | H | H | Cl | H | −14 | 6 | 1.5 | 18 | |
| 5 | H | H | H | Cl | −10±1 | 7 | 0.3 | 6 | |
| 6 | H | Br | H | H | −8±3 | 0.4 | 0.2 | 5 | |
| 7 | H | H | F | H | −27±3 | 6 | 2 | >10 | |
| 8 | H | $NO_2$ | H | H | 5±2 | 2 | 0.2 | >10 | |
| 9 | H | $NH_2$ | H | H | −10±14 | 50 | 6 | | |
| 10 | $CH_3$ | H | H | H | −37±8 | 0.5 | 0.1 | 0.6 | 76 |
| 11 | H | $CH_3$ | H | H | | 2 | 0.3 | >10 | |
| 12 | H | H | H | $CH_3$ | −22±10 | 4 | 3 | >10 | |
| 13 | OME | H | H | H | −20±14 | 0.5 | 0.2 | 4 | 19 |
| 14 | H | OME | H | H | −19±4 | 1 | 0.2 | 4 | 17 |
| 15 | H | H | H | OME | −16±3 | NA | NA | | |
| 16 | OME | OME | H | H | | 0.4 | | 0.7 | |
| 17 | H | OME | OME | H | +26 | 5 | | 4 | 0 |
| 18 | H | 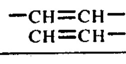 | | H | −25±12 | 0.7 | 0.07 | >50 | |
| 39 | —CH=CH—<br>CH=CH— | | H | H | −59 | — | — | — | — |

TABLE I-continued

| | R Position | | | | | | | | |
|---|---|---|---|---|---|---|---|---|---|
| | 7 | 8 | 9 | 10 | | | | | |
| 19 | H | H | H | H | −32±4 | 25 | 4 | | |
| 20 | Cl | H | H | H | −12±1 | 6 | 0.7 | 8 | |
| 21 | H | Br | H | H | Toxic | 3 | 1.5 | 9 | |
| 22 | $CH_3$ | H | H | H | −26±9 | 3 | 0.3 | >10 | |
| 23 | H | $CH_3$ | H | H | −7±2 | 16 | 2 | | |
| 24 | H | H | H | $CH_3$ | −19 | NA | NA | | |
| 25 | OME | H | H | H | −5±3 | 2 | 0.4 | 8 | |
| 26 | H | OME | H | H | −19±6 | 6 | 1.5 | >10 | |
| 27 | H | H | H | OME | +1±4 | NA | NA | | |
| 28 | H | OME | OME | H | +7±2 | NA | 32 | | |
| | R Position | | | | | | | | |
| | 6 | 7 | 8 | 9 | | | | | |
| 29 | H | H | H | H | −28 | 2 | | 7 | 35 |

+Denotes an increase in b.p.
−Denotes a decrease in b.p.

*In vivo/In vitro testing

Before dosing the animals, blood samples are taken. The blood is centrifuged to obtain the blood platelet-rich plasma. Aggregation of this plasma is induced with ADP or collagen. This is the control.

The animals are then dosed with the compounds to be tested (orally or parenterally). Depending upon the route of administration, one to two hours are allowed to elapse after dosing. Blood is drawn and the same procedure employed as for the control in untreated animals.

The dose required to produce 50% inhibition of the aggregation is determined by dose response data obtained in this manner.

EXAMPLE 1

Preparation of 3-(carbethoxymethyl)-3,4-dihydro-5-methyl-4-methylene-1-H-quinazolin-2-one (XIIIa)

To a solution of 22.4 g (0.15 mole) of 2-amino-6-methylacetophenone in toluene (750 ml) was added a solution of 19.4 g (0.15 mole) of ethyl isocyanatoacetate in toluene (150 ml). The system was fitted with a Dean-Stark trap and the solution heated to reflux. After the theoretical removal of water (3 hr), the solution was cooled to 0° overnight. The solution was filtered, the precipitate washed with cold toluene and dried yielding 33.9g (87% yield) of colorless crystals. Purification was effected by recrystallization from toluene; m.p. 151°–4°.

Anal. calc'd. for $C_{14}H_{16}N_2O_3$: C, 64.60; H, 6.20; N, 10.76, Found: C, 64.75; H, 6.24; N, 11.04.

EXAMPLE 2

Preparation of 3-(carbethoxymethyl)-4,5-dimethyl-1,2,3,4-tetrahydroquinazolin-2-one (XIVa)

To a suspension of 11.0 g (42 mmole) of 3-(carbethoxymethyl)-3,4-dihydro-5-methyl-4-methylene-1-H-quinazolin-2-one in 200 ml of 95% ethyl alcohol was added 1.0 g of 10% Pd/C catalyst and the mixture placed on a Paar hydrogenator. After theoretical hydrogen absorption, the solution was filtered under suction, the catalyst washed with ethyl alcohol and the solvent removed in vacuo affording 10.9 g (96% yield) of a colorless solid identified as the title compound.

EXAMPLE 3

Preparation of 2-chloro-3-carbethoxymethyl-4,5-dimethyl-2,4-dihydroquinazoline (XVa)

A mixture of 4.00 g (15.4 mmole) of 3-carbethoxymethyl)-4,5-dimethyl-1,2,3,4-tetrahydroquinazolin-2-one and 40 ml of phosphorus oxychloride was immersed in an oil bath (100°) for 1.5 hr. The solution was cooled, the excess phosphorus oxychloride removed under aspirator pressure and the residue dissolved in chloroform (100 ml). The chloroform solution was washed with an aqueous saturated sodium bicarbonate solution until the wash was neutral, the chloroform extract separated, dried (Mg $So_4$) and the solvent removed in vacuo affording 4.5 g of an oil. The spectral data was consistent with the title compound and the compound was used as such.

EXAMPLE 4

Preparation of 5,6-dimethyl-1,2,3,5-tetrahydroimidazo[2,1-b]quinazolin-2-one (50) (Ia)

To a solution of 4.3 g (15.4 mmole) of 2-chloro-3-(carbethoxymethyl)-4,5-dimethyl-3,4-dihydroquinazoline in 50 ml of absolute ethanol was added a solution of 2.0 g (120 mmole) of ammonia in 25 ml of absolute ethanol, the system was stoppered and immersed in an oil bath (100°). After 16 hrs. of heating, the solution was cooled, the solvent removed in vacuo and the residue crystallized from 1N hydrochloric acid affording 2.29 g (59% yield) of yellow crystals mp 235°–40°.

Anal. calc'd. for $C_{12}H_{13}N_3O.HCl$: C, 57.26; H, 5.61; N, 16.69, Found: C, 57.08; H, 5.56; N, 16.82.

EXAMPLE 5

Preparation of 3-(carbethoxymethyl)-3,4-dihydro-6-methyl-4-methylene-1-H-quinazolin-2-one (XIIIb)

Substitution in the procedure of example 1 for the 2-amino-6-methylacetophenone used therein of an equimolar quantity of 2-amino-5-methylacetophenone produced the title compound; m.p.

Anal. calc'd. for $C_{14}H_{16}N_2O_3$: C, 64.60; H, 6.20; N, 10.76, Found: C, 64.89; H, 6.26; N, 10.99.

EXAMPLE 6

Preparation of 3-(carbethoxymethyl)-4,6-dimethyl-1,2,3,4-tetrahydroquinazolin-2-one (XIVb)

Substitution in the procedure of example 2 for the 3-(carbethoxymethyl)-3,4-dihydro-5-methyl-4-methylene-1-H-quinazolin-2-one used therein of an equimolar quantity of 3-(carbethoxymethyl)-3,4-dihydro-6-methyl-4-methylene-1-H-quinazolin-2-one produced the title product; m.p. 113°–114.5° C; 98% yield.

Anal. calc'd. for $C_{14}H_{16}N_2O_3$: C, 64.10; H, 6.92; N, 10.68, Found: C, 64.56; H, 6.87; N, 10.97.

EXAMPLE 7

Preparation of 2-chloro-3-carbethoxymethyl-4,6-dimethyl-3,4-dihydroquinazoline (XVb)

Substitution in the procedure of example 3 for the 3-(carbethoxymethyl)-4,5-dimethyl-1,2,3,4-tetrahydroquinazolin-2-one used therein of an equimolar quantity of 3-(carbethoxymethyl)-4,6-dimethyl-1,2,3,4-tetrahydroquinazolin-2-one produced the title compound as an oil which was used as such in the next example.

EXAMPLE 8

Preparation of 5,7-Dimethyl-1,2,3,5-tetrahydroimidazo[2,1-b]quinazolin-2-one (51) (Ib)

Substitution in the procedure of example 4 for the 2-chloro-3-(carbethoxymethyl)-4,5-dimethyl-3,4-dihydro-quinazoline used therein of an equimolar quantity of 2-chloro-3-(carbethoxymethyl)-4,6-dimethyl-3,4-dihydroquinazoline produced the title product; m.p. 265°–70° C. in 47% yield.

Anal. calc'd. for $C_{12}H_{13}N_3O.HCl$: C, 57.26; H, 5.61; N, 16.69, Found: C, 57.12; H, 5.62; N, 16.42.

EXAMPLE 9

Preparation of 5-methyl-3-(carbethoxymethyl)-1,2,3,4-tetrahydroquinazolin-2-one (XIVc).

To a cooled solution of 15.00 g (67 mmole) of N-(2-amino-6-methyl benzyl) glycine ethyl ester in 300 ml of anhydrous tetrahydrofuran under a nitrogen atmosphere was added a solution of 11.72 g (72 mmole) of 1,1'-carbonyldiimidazole in 200 ml of anhydrous tetrahydrofuran at such a rate that the temperature did not exceed 5°. Upon complete addition, the solution was allowed to stir at room temperature for 2 hrs., heated to reflux for 18 hrs., cooled to room temperature and the tetrahydrofuran removed in vacuo. The residue was dissolved in methylene chloride (250ml), washed with 5% aqueous hydrochloric acid (2 × 100 ml), then water (100 ml). The methylene chloride extract was dried ($Na_2SO_4$) and the solvent removed in vacuo affording 14.0 g (83% yield) of a colorless solid. Purification was effected by crystallization from nitromethane; mp 184°–5°.

Anal. calc'd. for $C_{13}H_{16}N_2O_3$: C, 62.89; H, 6.50; N, 11.28, Found: C, 62.85; H, 6.45; N, 11.22.

EXAMPLE 10

Preparation of 2-Chloro-3-carbethoxymethyl-5-methyl-3,4-dihydroquinazoline hydrochloride (XVc).

A mixture of 2.45 g (10 mmole) of 5-methyl-3-carbethoxymethyl-1,2,3,4-tetrahydroquinazolin-2-one and 20 ml of phosphorus oxychloride was immersed in an oil bath (105°–110°) for 3.5 hr. The solution was cooled, the excess phosphorus oxychloride removed under aspirator pressure and the residue dissolved in chloroform (50 ml). Ice water was added, the mixture shaken and 40% sodium hydroxide was added dropwise to attain a pH=6. The above process was repeated until a pH=6 was maintained after shaking, the chloroform extract was separated, dried ($Na_2SO_4$) and the solvent removed in vacuo. The residue was dissolved in ethyl acetate (100 ml), the solution saturated with hydrogen chloride gas and the mixture heated to gentle boiling for 10 mins. The mixture was filtered while hot and the precipitate dried yielding 2.11 g (70% yield) of a pale yellow powder. Purification was effected by crystallization from acetonitrile; mp 199–201.

Anal. calc'd. for $C_{13}H_{15}ClN_2O_2HCl$: C, 51.52; H, 5.28; N, 9.24, Found: C, 51.87; H, 5.28; N, 9.27.

EXAMPLE 11

Preparation of 6-methyl-1,2,3,5-tetrahydroimidazo-[2,1-b]quinazolin-2-one (12) (Ic)

To a solution of 0.60 g (2 mmole) in 20 ml of absolute ethyl alcohol was added 1.36 g (4 mmole) of a 5% ammonia/ethyl alcohol stock solution, the system stoppered and immersed in an oil bath (100°). After 16 hrs. of heating, the solution was cooled, the solvent removed in vacuo and the residue suspended in water (30 ml). The mixture was made basic (pH9) by the addition of saturated sodium bicarbonate solution, the mixture stirred at room temperature and filtered. The precipitate was washed with water, then isopropyl alcohol and dried yielding 0.32 g (80% yield) of a colorless powder. The spectral properties (ir and nmr) were identical to the known 6-methyl-1,2,3,5-tetrahydroimidazo-[2,1-b]quinazolin-2-one.

EXAMPLE 12

Preparation of 3-(Carbethoxymethyl)-3,4-dihydro-5-chloro-4-methylene-1-H-quinazolin-2-one (XIIId)

Substitution in the procedure of example 1 for the 2-amino-6-methylacetophenone used therein of an equimolar quantity of 2-amino-6-chloroacetophenone produced the title product in 60% yield; m.p. 129–138°C.

Anal. calc'd. for $C_{13}H_{13}ClN_2O_3$: C, 55.62; H, 4.67; Cl, 12.63; N, 9.98, Found: C, 55.65; H, 4.68; Cl, 12.28; N, 10.13.

EXAMPLE 13

Preparation of
3-(Carbethoxymethyl)-3,4-dihydro5-chloro-4-methyl-1H-quinazolin-2-one (XIVd)

Substitution in the procedure of example 2 for the 3-(carbethoxymethyl)-3,4-dihydro-5-methyl-4-methylene-1H-quinazolin-2-one used therein of an equimolar quantity of compound XIIId produced the title compound in 42% yield; m.p. 143°–143.5°C.

Anal. calc'd. for $C_{13}H_{15}ClN_2O_3$: C, 55.23; H, 5.35; Cl, 12.54; N, 9.91, Found: C, 55.26; H, 5.18; Cl, 12.34; N, 9.99.

EXAMPLE 14

Preparation of
2-Chloro-3-(carbethoxymethyl)-5-chloro-4-methyl-3,4-dihydroquinazoline (XVd)

Substitution in the procedure of example 3 for the compound XIVa used therein of an equimolar quantity of XIVd produced the title compound XVd.

EXAMPLE 15

Preparation of
6-chloro-5-methyl-1,2,3,5-tetrahydroimidazo[2,1-b]quinazolin-2-one (Id)

Substitution in the procedure of example 4 for the compound XVa used therein of a equimolar quantity of compound XVd produced the title compound in 20% yield; m.p. 252°C. with decomp. (as the hydrochloride salt).

Anal. calc'd. for $C_{11}H_{10}ClN_3O.HCl. 1/2H_2O$: C, 47.00; H, 4.30; Cl, 25.22; N, 14.95, Found: C, 46.59; H, 4.40; Cl, 25.08, N, 14.87.

EXAMPLE 16

Preparation of
3-(Carbethoxymethyl)-3,4-dihydro-5-methoxy-4-methylene-1H-quinazolin-2-one (XIIIe)

Substitution in the procedure of example 1 for the 2-amino-6-methylacetophenone used therein of an equimolar quantity of 2-amino-6-methoxyacetophenone produced the title product in 73% yield; m.p. 148.5° - 149°C.

Anal. calc'd. for $C_{14}H_{16}N_2O_4$: C, 60.86; H, 5.84; N, 10.14, Found: C, 60.56; H, 5.80; N, 10.10.

EXAMPLE 17

Preparation of
3-(Carbethoxymethyl)-5-methoxy-4-methyl-1,2,3,4-tetrahydroquinazolin-2-one (XIVe)

Substitution in the procedure of example 2 for the compound XIIIa used therein of an equimolar quantity of compound XIIIe produced the title compound in 77% yield; m.p. 150.5° - 151°C.

Anal. calc'd. for $C_{14}H_{18}N_2O_4$: C, 60.42; H, 6.52; N, 10.06, Found: C, 60.49; H, 6.32; N, 9.91.

EXAMPLE 18

Preparation of
2-Chloro-3-(Carbethoxymethyl)-5-methoxy-4-methyl-3,4-dihydroquinazoline (XVe)

Substitution in the procedure of example 3 for the compound XIVa used therein of an equimolar quantity of compound XIVe produced the title compound.

EXAMPLE 19

Preparation of
6-Methoxy-5-methyl-1,2,3,5-tetrahydroimidazo[2,1-b]quinazolin-2-one (Ie)

Substitution in the procedure of example 4 for the compound XVa used therein of an equimolar quantity of XVe produced the title compound in 60% yield; m.p. 250° C. (The hydrochloride salt; with decomposition).

Anal. calc'd. for $C_{12}H_{13}N_3O_2.HCl.H_2O$: C, 50.44; H, 5.64; Cl, 12.41; N, 14.71, Found C, 50.51; H, 5.42; Cl, 12.32; N, 14.76.

We claim:

1. The process for the preparation of the compound having the formula

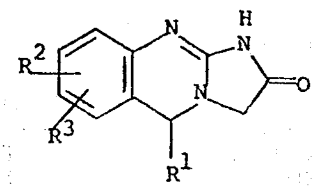

in which $R^1$ is (lower)alkyl, $R^2$ and $R^3$ are alike or different and each is hydrogen, chloro, bromo, fluoro, $SO_3H$, (lower)alkyl, hydroxy, nitro, amino, (lower)alkoxy or phenyl, or when taken together $R^2$ and $R^3$ are methylenedioxy or the moiety —CH=CH—CH=CH—; which process comprises the consecutive steps of A. mixing a 2-aminoacetophenone having the formula

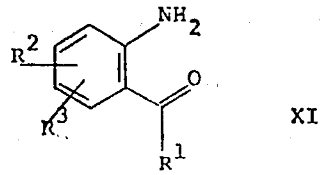

in which $R^1$, $R^2$ and $R^3$ are as described above, with a (lower)alkyl isocyanatoacetate having the formula

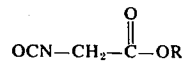

in which $R^4$ is (lower)alkyl of 1 to 6 carbon atoms, in a molar ratio of at least one mole of compound XII per mole of compound XI, with the aid of heat in the presence of a reaction inert organic solvent, to produce the compound having the formula

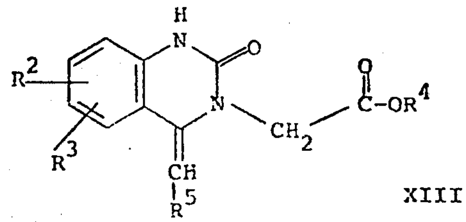

in which $R^2$, $R^3$ and $R^4$ are as above and $R^5$ is H or (lower)alkyl of 1 to 5 carbon atoms;

B. hydrogenating compound XIII with hydrogen in the presence of a metal catalyst selected from the group consisting of palladium, platinum, Raney nickel, rhodium, ruthenium, nickel and palladium on charcoal, in a (lower)alkanol or water-(lower-)alkanol solvent system to produce the compound having the formula

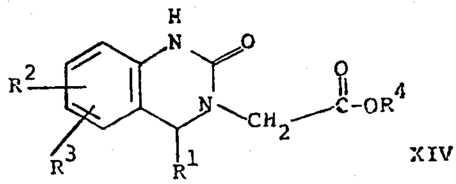

in which $R^1$, $R^2$, $R^3$ and $R^4$ are as above;

C. halogenating compound XIV with a halogenating agent selected from the group consisting of phosphorous oxychloride, $POBr_3$, phosphorous pentachloride and thionyl chloride, in a ratio of at least one mole of halogenating agent per mole of compound XIV, in the presence of a reaction inert organic solvent if needed, to produce the compound having the formula

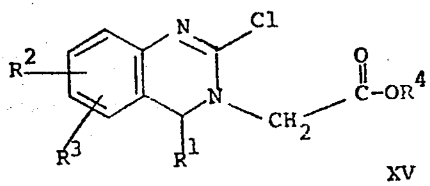

in which $R^1$, $R^2$, $R^3$ and $R^4$ are as above; and

D. treating compound XV with a large excess of ammonia, with the aid of heat, to produce the compound of formula I.

2. The process of claim 1 which comprises the consecutive steps of

A. mixing a 2-aminoacetophenone having the formula

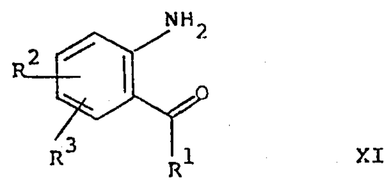

in which $R^1$ is (lower)alkyl, $R^2$ and $R^3$ are alike or different and each is hydrogen, chloro, bromo, fluoro, (lower)alkyl, hydroxy, nitro, amino, (lower)alkoxy or phenyl, or when taken together $R^2$ and $R^3$ are methylenedioxy or the moiety —CH═CH—CH═CH— ; with a (lower)alkyl isocyanatoacetate having the formula

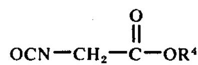

in which $R^4$ is (lower)alkyl of 1 to 3 carbon atoms in a molar ratio of about 1 to 1.5 moles of compound XII per mole of compound XI, in an organic solvent capable of forming an azeotrope, which solvent is selected from the group consisting of benzene, toluene and xylene, separating the water so generated, to produce the compound having the formula

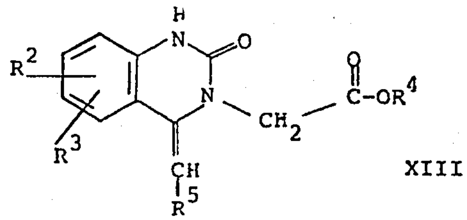

in which $R^2$, $R^3$, $R^4$ are as above and $R^5$ is H or (lower)-alkyl of 1 to 5 carbon atoms;

B. hydrogenating compound XIII with hydrogen in the presence of a catalyst selected from the group consisting of palladium, platinum, Raney nickel, rhodium, ruthenium, nickel and palladium on charcoal in a (lower)alkanol or (lower)alkanol-water solvent system, to produce the compound having the formula

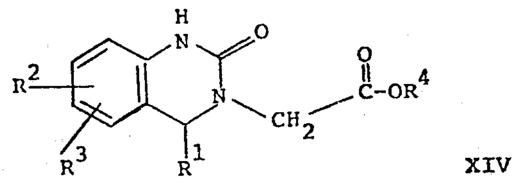

in which $R^1$, $R^2$, $R^3$ and $R^4$ are as above;

C. halogenating compound XIV with a halogenating agent selected from the group consisting of phosphorous oxychloride, $POBr_3$, phosphorous pentachloride and thionyl chloride, in a ratio of at least one mole of halogenating agent per mole of compound XIV, in the presence of a reaction inert organic solvent, if needed, to produce the formula

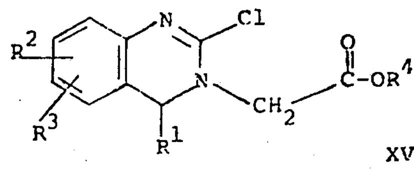

in which $R^1$, $R^2$, $R_3$ and $R^4$ are as above; and

D. treating compound XV with a large excess of ammonia dissolved in a (lower)alkanol, with the aid of heat in a sealed vessel, to produce compound I.

3. The process of claim 1 which comprises the consecutive steps of

A. mixing a 2-aminoacetophenone having the formula

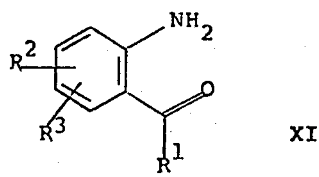

in which $R^1$ is (lower)alkyl of 1 to 3 carbon atoms, $R^2$ and $R^3$ are alike or different and are hydrogen, chloro, bromo, fluoro, (lower)alkyl of 1 to 3 carbon atoms, hydroxy, nitro, amino, (lower)alkoxy or phenyl, or when taken together $R^2$ and $R^3$ are methylenedioxy or the moiety —CH═CH—CH═CH—; with a (lower)alkyl isocyanatoacetate having the $$\text{OCN—CH}_2\text{—}\overset{\text{O}}{\overset{\|}{\text{C}}}\text{—OR}^4 \qquad \text{XII}$$

in which $R^4$ is (lower)alkyl of 1 to 2 carbon atoms, in a molar ratio of about 1 to 1.2 moles of compound XII per mole of compound XI, in an organic solvent capable of forming an azeotrope, which solvent is selected from the group consisting of benzene, toluene and xylene, separating the water so generated, to produce the compound having the formula

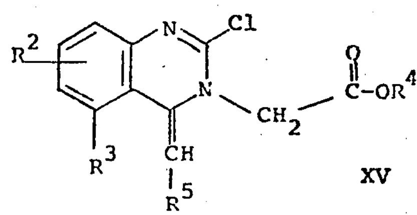

in which $R^2$, $R^3$, $R^4$ are as above and $R^5$ is H or (lower)alkyl of 1 to 2 carbon atoms;

B. hydrogenating compound XIII with hydrogen in the presence of a catalyst selected from the group consisting of palladium, platinum, Raney nickel, rhodium, ruthenium, nickel, and palladium on charcoal in a (lower)alkanol or (lower)alkanolwater solvent system, to produce the compound having the formula

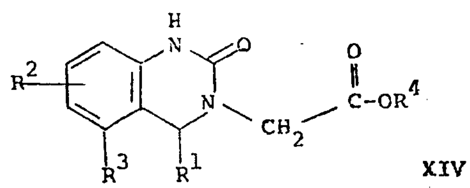

in which $R^1$, $R^2$, $R^3$ and $R^4$ are as above;

C. chlorinating compound XIV with a chlorinating agent selected from the group consisting of phosphorous oxychloride, phosphorus pentachloride and thionyl chloride, in a ratio of two to ten moles of chlorinating agent per mole of compound XIV, in the presence of a reaction inert organic solvent if needed, to produce the compound having the formula

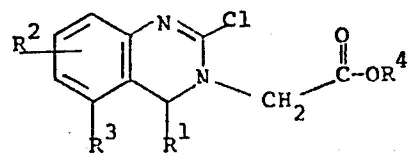

in which $R^1$, $R^2$, $R^3$ and $R^4$ are as above; and

D. treating compound XV with a large excess of ammonia dissolved in a (lower)alkanol, with the aid of heat in a sealed vessel to produce compound I.

4. The process for the preparation of the compound having the formula

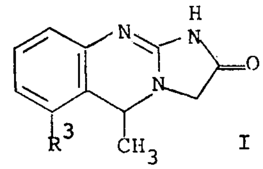

in which $R^3$ is methyl, methoxy or chloro, which process comprises the consecutive steps of A. heating a 2-aminoacetophenone having the formula

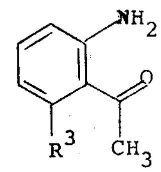

in which $R^3$ is methyl, methoxy or chloro, with a (lower)alkyl isocyanatoacetate having the formula

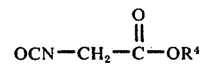

in which $R^4$ is methyl or ethyl in a molar ratio of about 1 to 1.1 moles of compound XII per mole of compound XI, in toluene at reflux temperature, separating the water so generated, to produce the compound having the formula

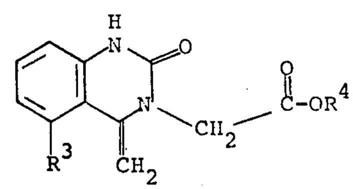

in which $R^3$ and $R^4$ are as above;

B. hydrogenating compound XIII with hydrogen in the presence of 5 to 10% palladium on charcoal, with mixing, in 95% ethanol to produce the compound having the formula

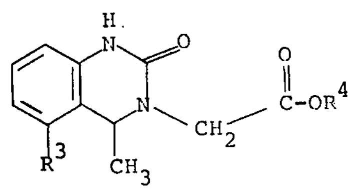

in which $R^3$ and $R^4$ are as above;

C. chlorinating compound XIV by dissolving it in a large molar excess of phosphorous oxychloride, followed by heating at about 70° C to about 115° C for about 1 to 2 hours, following which the excess phosphorous oxychloride is removed in vacuo to produce the compound having the formula

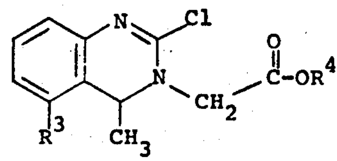

XV in which $R^3$ and $R^4$ are as above; and

D. treating compound XV with a large excess of ammonia dissolved in a (lower)alkanol, with the aid of heat in a sealed vessel to produce compound I.

* * * * *